United States Patent [19]

Lerman

[11] 4,070,483

[45] Jan. 24, 1978

[54] METHOD OF ADMINISTERING A HUMAN OCULAR TREATING AGENT AND PRODUCT THEREFOR

[76] Inventor: Sidney Lerman, 1648 Musket Ridge Road, NW., Atlanta, Ga. 30327

[21] Appl. No.: 697,918

[22] Filed: June 21, 1976

Related U.S. Application Data

[63] Continuation-in-part of Ser. No. 591,758, June 30, 1975, abandoned.

[51] Int. Cl.² .......................................... A61K 31/195
[52] U.S. Cl. .................................................. 424/319
[58] Field of Search ........................................ 424/319

[56] References Cited

PUBLICATIONS

Chvapil et al.,–Chem. Abst., vol. 68 (1968), p. 76814t.
Barron et al.,–Chem. Abst., vol. 77 (1972), p. 14316j.

Primary Examiner—Sam Rosen
Attorney, Agent, or Firm—Newton, Hopkins & Ormsby

[57] ABSTRACT

A method of administering an agent to the ocular lens of animals for the treatment of an aging parameter and nuclear cataracts therein which includes the steps of preparing a solution of D,L-penicillamine; exposing an artificial ocular contact lens to the solution such that the compound is retained on the artificial lens; and contacting the animal lens with the artificial lens so that the compound is absorbed into the animals lens. Another method is to incorporate the compound in a timed-release carrying agent and place the agent in the inferior cul de sac of the eye.

8 Claims, 11 Drawing Figures

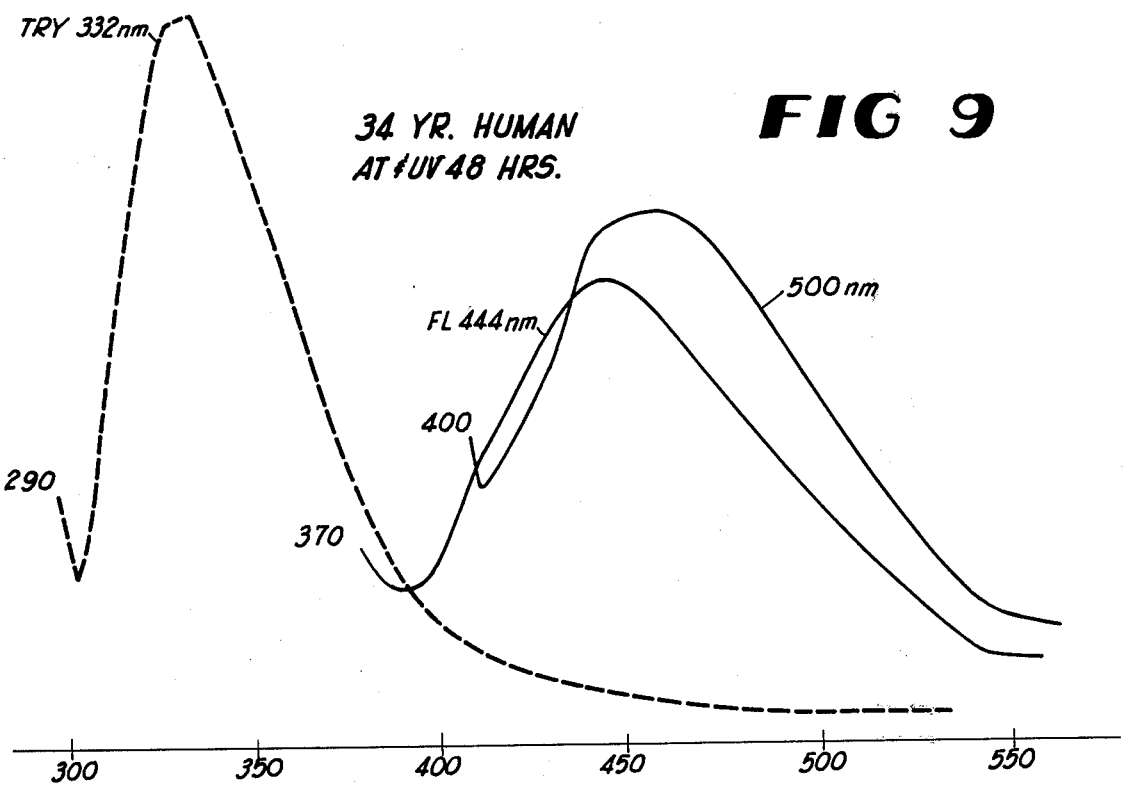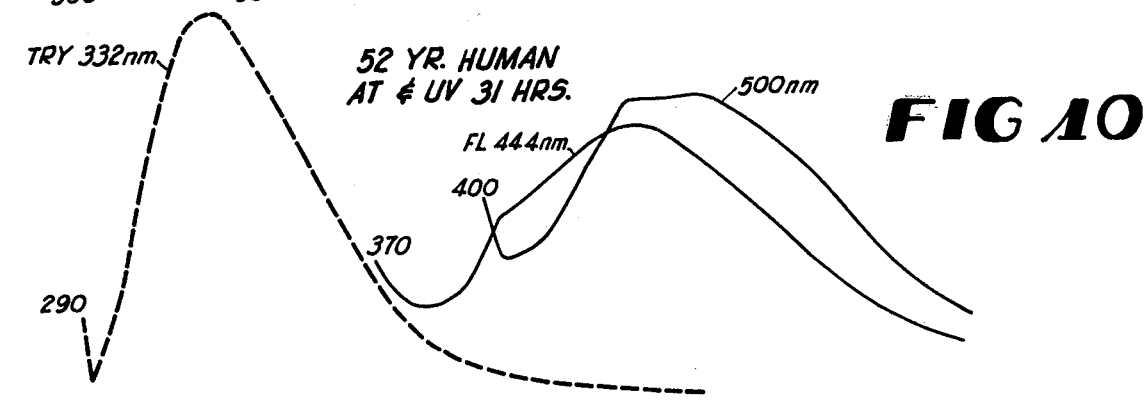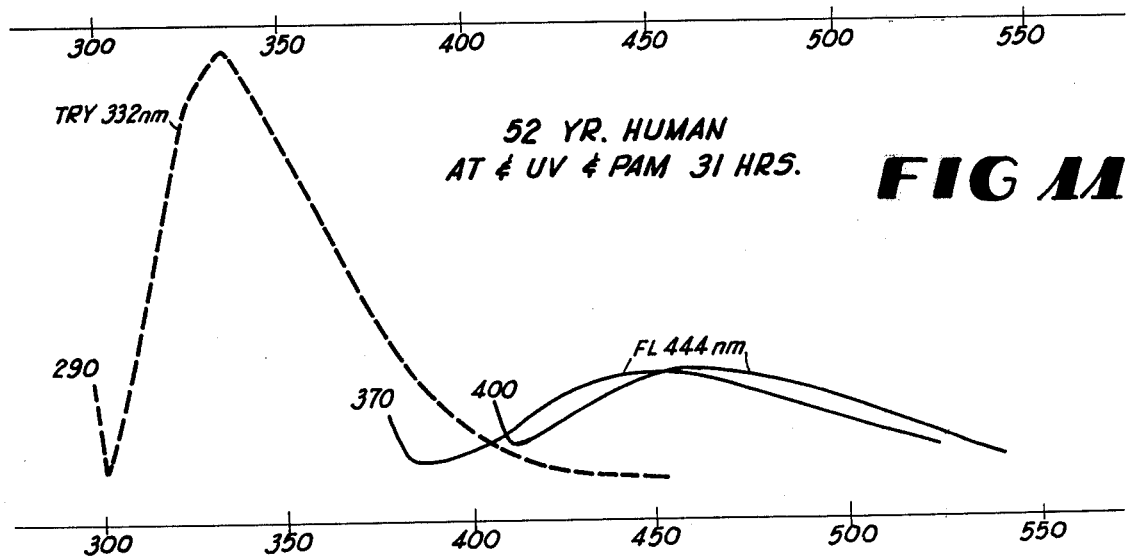

METHOD OF ADMINISTERING A HUMAN OCULAR TREATING AGENT AND PRODUCT THEREFOR

CROSS-REFERENCE TO RELATED APPLICATION

This is a continuation-in-part of my application, Ser. No. 591,758, filed June 30, 1975, now abandoned.

BACKGROUND OF THE INVENTION

This invention relates to the treatment of the eyes of animals and, more particularly, to a method of administering a ocular treating agent and product therefor.

The ocular lens proteins have for many years been classified into the water soluble fractions and the water insoluble fractions. It is generally accepted that the newborn lens consists almost entirely of water soluble proteins and that as the lens matures and grows older, there is a slow progressive accumulation of the water insoluble protein fraction with a corresponding relative decrease in the total concentration of water soluble proteins. In the newborn rat and human lens, the soluble proteins account for more than 95% of the total protein fraction of the lens, but as the lens ages there is a progressive increase in the relative concentration of insoluble protein until it reaches a level of over 50% in the old rat lens and approximately 40% in the agend human lens.

There is also a correlation between the increase in the level of water insoluble lens protein and the development of presbyopia in the human lens. Presbyopia is associated with an increase in the size of the central core of the lens, the development of the so-called nuclear sclerosis. Nuclear sclerosis can proceed at various rates and in some people is progresses to the formation of nuclear cataracts. The human lens also develops a yellow color of increasing intensity as it ages with the extreme being the advanced brown or black nuclear cataracts.

SUMMARY OF THE INVENTION

An object of this invention is to inhibit the generation of fluorogens and the formation of the water insoluble lens protein and nuclear cataracts in the ocular lens.

Another object of the present invention is to provide a method of administering an agent to the ocular lens which will prevent the formation of an aging parameter and nuclear cataracts therein and product therefor.

Another object of the present invention is to provide an improved composition for cleansing artificial contact lenses.

The foregoing and other objects are obtained in accordance with the present invention wherein an agent is provided to be administered to the ocular lens by soaking artificial contact lenses in a solution of the agent until it is absorbed on and into the artificial lens, whereby the agent enters the eye upon the artificial lens being placed on the ocular lens. The agent is a water soluble, non-toxic, anti-oxidant, free-radical scavenging compound having a molecular weight of 150 to 12,000 and at least one sulfhydril group thereon. The preferred compound has been found to be D,L-penicillamine. The solution also may contain an antiseptic material, the preferred one being from 0% to 0.1% of the sodium salt of ethylmercurithiosalicylic acid.

Another method of administering the agent is to incorporate it within a sustained release carrier, such as a hydrophylic gel or hydrophylic-hydrophobic gel or in an insert, and placing it within the inferior cul de sac of the eye. The agent may also be applied to the eye in an ointment form or as eye drops.

BRIEF DESCRIPTION OF THE FIGURES OF DRAWINGS

FIGS. 9 and 10 are graphs of fluorescence spectroscopic results on human lens exposed to ultraviolet light and aminotrizazole; and FIG. 11 is a graph of fluorescence spectroscopic results on human lens exposed to ultraviolet light, aminotrizazole and D,L-penicillamine.

DESCRIPTION OF THE INVENTION

Figure 1:
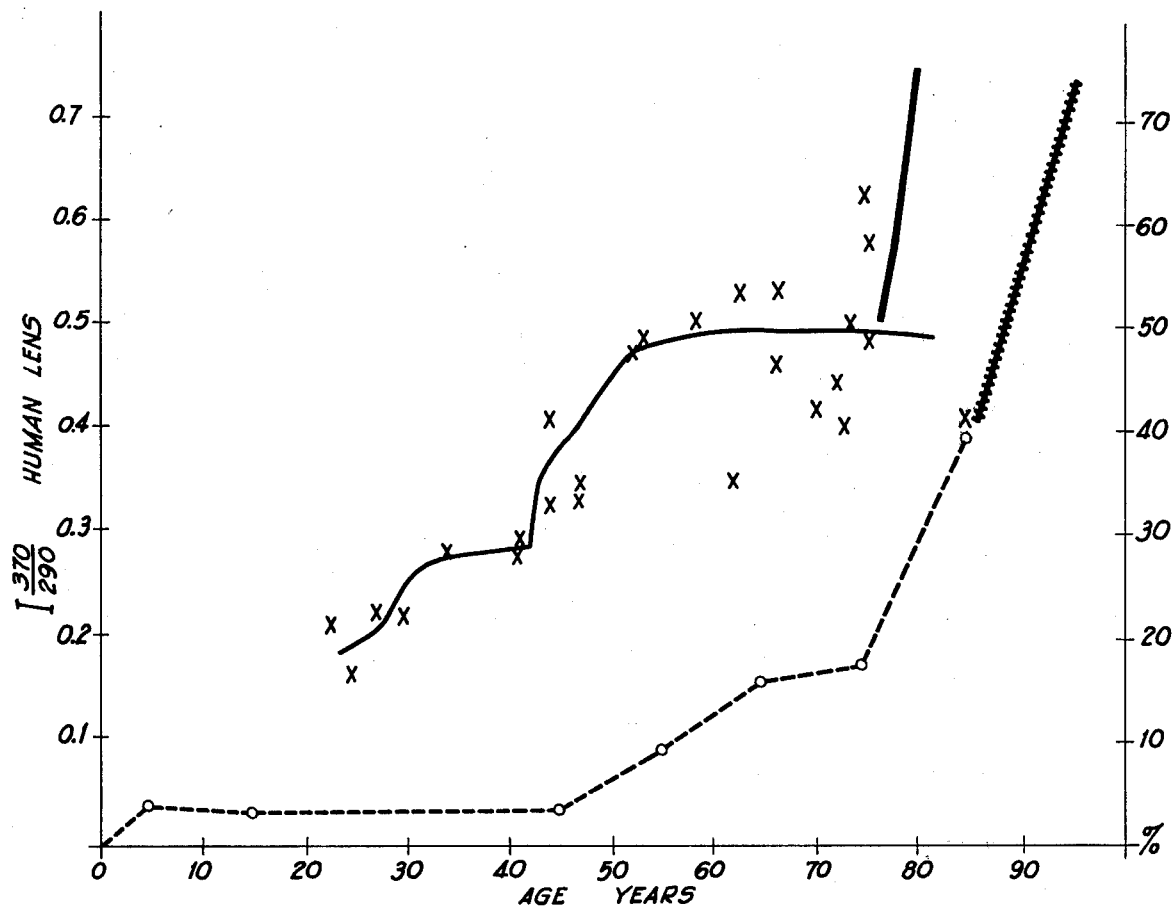
FIG. 1 is a graph of the results of fluorescence spectroscopy on normal human lens ranging in age from 3 days to 88 years.

Recent studies have shown that the yellow color in a lens is due (at least in part) to the presence of at least one fluorogen (fluorescent compound) associated with one or more of the protein fractions of the ocular lens. This fluorogen has an activation peak at 360 – 370 nm and an emission peak at 440 nm, as compared with protein-bound trytophan which has a 290 nm activation peak and a 332 nm emission peak. This fluorogen shows a direct age relationship, being absent in the young lens, increasing markedly in concentration in the human lens when presbyopia develops and reaching a peak in advanced nuclear sclerosis and nuclear cataracts. The increase in this fluorogen is so directly related to the age of the lens that such spectra can serve as aging parameters (i.e. that phenomenon which indicates comparable age in a lens). The increase in the water insoluble lens protein (which is considered to be another aging parameter) is preceded by the increase in the fluorogen content of the lens.

This fluorogen has been postulated to be derived from one or more of the aromatic amino acids in the soluble lens proteins by means of a photo-oxidation reaction resulting in the generation of a specific fluorogen tightly bound to at least one peptide within the protein. Tryptophan is considered to be the most likely candidate proposed as the fluorogen. The process would be initiated by prolonged exposure of the lens to ultraviolet light between 295 and 380 nm. While the cornea filters out almost all of the ultraviolet light of wavelength less than 295 nm, the lens is constantly exposed to the longer ultraviolet radiation.

Ultraviolet light and ionizing radiation are capable of generating free radicals. It is accepted by many investigators that aging itself must be due at least in part to damage caused by radical reactions within tissues. An important effect of the induction of a free radical state in a compound by ultraviolet light (or other physical agents) is the fact that the resulting free radicals have considerably altered physical chemical properties leading to an alteration in their function. It has also been shown that proteins can be significantly altered by radical reactions with the aromatic amino acid residues in the proteins being particularly susceptible. Thus prolonged exposure of the ocular lens to long UV radiation could result in free radical formation and the generation of one or more fluorogens in increasing concentrations. It is therefore conceivable that the initiating process in the formation of the fluorogen in the lens could be due to its prolonged exposure to long ultraviolet radiation throughout life. By means of an ultraviolet-induced free-radical mechanism, the fluorogen induces polymerization and insolubilization of some of the previously soluble lens proteins, leading to the aging of the lens and nuclear cataract formation.

The progressive increase in the fluorogen is paralleled by a similar increase in the relative concentration of the insoluble fraction with age. In vitro studies with lens incubates (mouse, rat and human lenses) have demonstrated that this fluorogen can be induced and/or markedly accelerated in lens incubation systems in which the lenses are exposed to 3-aminotriazole (AT) and ultraviolet radiation. The resultant depletion of an important free radical scavenger in the lens (glutathione) increases its sensitivity to UV radiation, thereby accelerating the photo-induced fluorogen formation.

In order to inhibit or prevent the increase in fluorogen concentration and the polymerization of the soluble lens proteins, an agent must be administered to the ocular lens which will "mop up" the free radicals generated within the lens because of its exposure to ultraviolet light between 295 and 380 nm wavelength. The agent must also be non-toxic, water soluble, possess chelating properties and should also be anti-oxidant and not metabolize easily. Further, the compound should have a relatively small molecular weight (from 150 to 12,000) so that it may enter the lens through the capsule of the lens and then through the cellular membrane. The compound must also possess the characteristic of being able to pass the blood aqueous barrier, so that it can be administered through the bloodstream to the eye. In order to prevent the rejection of the compound by the body, the compound should also be an analogue of a natural biological compound.

It has been found that D,L-penicillamine is an excellent free radical scavenger and is much less toxic than other known free radical scavengers, such as cysteine and cysteamine. The compound has already been utilized to treat a different disease process, that of Wilson's disease which is a degeneration of the liver due to an abnormal copper metabolism; the function of D,L-penicillamine in the treatment of Wilson's disease is to act as a chelating agent to remove the copper deposits found in various organs of the body and to prevent the formation of further deposits.

The below described experiments demonstrate that there is a direct relationship between the formation and relative emission intensity of the fluorogen and the age of the lens; and also demonstrate the induction and/or increasing concentration of this fluorogen in normal human lens by exposing them to ultraviolet light (290 – 380 nm) for varying periods of time in a lens incubation system. Having defined and proven the molecular basis of aging and the formation of the aging nuclear cataract (including the brown and black cataract) in man, the experiments have also demonstrated that D,L-penicillamine can dramatically prevent this phenomenon.

MATERIALS AND METHODS

Human lenses were obtained from the Lions Eye Bank of Atlanta and the Florida Lions Eye Bank of Miami. Both fresh and frozen lenses were utilized for fluorescence spectroscopy since it was determined that reproducible data could be obtained in stored frozen lenses which were thawed immediately preceding spectroscopy as compared with a fresh lens prior to freezing. Fresh lenses were utilized in the incubation system which consisted of a balanced salt solution (bicarbonate buffer) containing 7 mM glucose, 0.75 mM L-glutamine, 2 mg% potassium penicillin G and streptomycin sulfate, and it was gassed with a mixture of 95% oxygen-5% $CO$.

The long wave ultraviolet light utilized in the incubation experiments was produced by General Electric black light fluorescence lamps, F15T8BLB. Lamp output was measured by a J-221 Blak-Ray ultraviolet meter which is sensitive to light of 300 to 400 nm wavelength with a peak sensitivity at approximately 365 nm where the maximum output of this lamp occurs. Single lenses were also exposed to monochromatic U.V. radiation at specific wave lengths (280, 290, 300, 320, and 340 nm, respectively) and were incubated for periods of time ranging from 4 – 24 hrs. The incubation temperature was maintained at 37° $C(\pm 1°)$. For the in vitro experiments, 10 mM 3-aminotriazole (AT) was added to the incubation media where required and for the in vivo mouse experiments, 0.35 ml of 20% 3-aminotriazole was administered daily to the post-weanling mice by intraperitoneal injections. AT is a catalase (peroxidase) inhibitor; thus, more glutathione is being used up by the lens and a significant decrease in the concentration of glutathione in lenses incubated with AT has been shown. The resultant depletion of an important free radical scavenger in the lens increases its sensitivity to UV radiation, thereby accelerating the photo-induced fluorogen formation. In the experiments relating to the effects of D-penicillamine, a total of 10 mM D,L-penicillamine was added to each incubation mixture. Fluorescence spectroscopy was performed according to the methods described in the literature.

It should be noted that in all the in vitro lens incubation experiments, control studies were performed in which the lenses were incubated with AT alone but were shielded from ultraviolet light or incubated solely in the incubation medium without AT and UV. None of those control lenses developed any fluorogen or showed any increase in the amount of fluorogen present prior to incubation.

Results

The results of fluorescence spectroscopy on normal human lenses ranging in age from 3 days to 88 years are shown in FIG. 1. Normal human lenses are shown in solid line and nuclear cataracts are shown in heavy solid line and are compared with the relative percent of insoluble lens protein in comparably aged lenses (dashed line) and in nuclear cataracts (heavy dashed line). Excitation at 280 – 300 nm gave emission spectra characteristic of protein bound tryptophan (332 nm) in lenses of all ages. Excitation between 350 – 400 nm reveals the presence of a second fluorogen with an emission peak at 444 nm and an excitation max at 360 – 370 nm. This fluorogen is not present within the first year of life (and perhaps not within the first decade) and then appears in relatively low concentration, progressively increasing till the end of the fourth decade at which time there is a relatively marked increase in the I (370/290) ratio which reaches levels approximately 2 – 3 times those present in the prepresbyopic age groups. It should be noted that the highest levels of the fluorogen are present in lenses in which nuclear sclerosis can be observed. The age-related increase in the water insoluble lens protein appears to be paralleled as well as preceded by the age-related increase in the 444 nm fluorogen.

The foregoing data was plotted as the I (370/290); that is, the emission intensity at 444 nm of the fluorogen (activation at 370 nm) over the fluorescence emission intensity of the intrinsic protein bound tryptophan 332 nm (activation 290 nm). This ratio is utilized since protein-bound tryptophan could be demonstrated in lenses of all ages (which is not the case with the fluorogen), and also because there is the suggestion of an inverse relationship between the fluorescence intensity of tryptophan and this fluorogen in the lens. FIG. 1 also demonstrates the marked increase both in the insoluble lens protein concentration and in the fluorogen in the advanced brown nuclear cataracts.

Results were also obtained from rat lens incubations ranging from 17 to 96 hours. There was no fluorogen present in lenses obtained from such young rats, but when these lenses are incubated for varying periods of time and exposed to AT and UV, there was a significant generation of the fluorogen at 17 hours with a very marked increase in its relative concentration occurring after 30 hours of incubation. The effects of adding D,L-penicillamine to such incubates were also demonstrated. No fluorogen could be generated up to 30 hours of incubation and less than 10% of the fluorogen could be generated in such a system after 96 hours incubation, as compared with a similar system in which the D,L-penicillamine was omitted.

Figure 2:
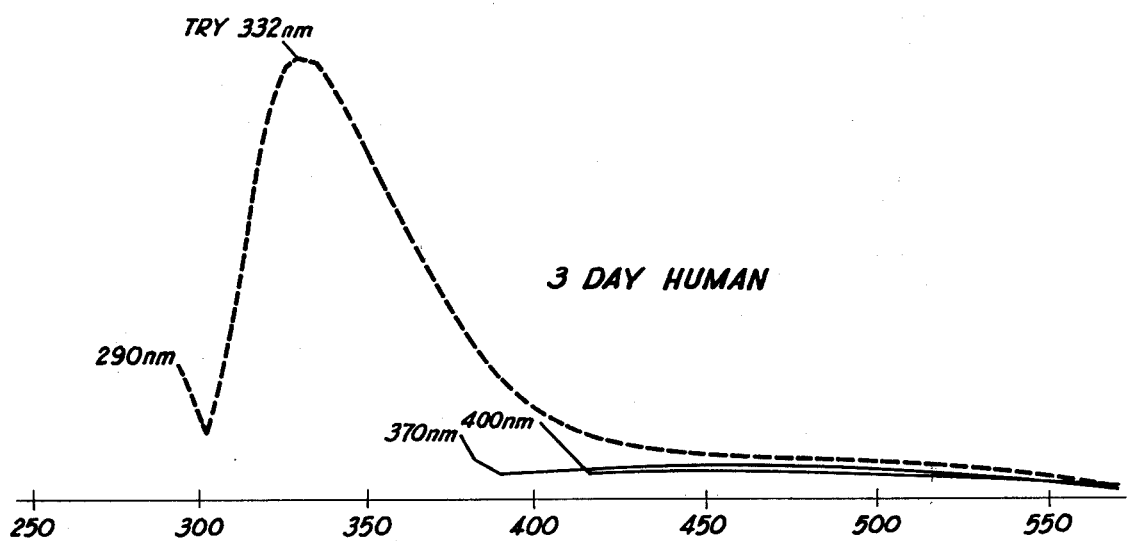
FIGS. 2 - 8 are graphs of fluorescence spectroscopic results of in vitro incubation experiments with human lens.
Figure 3:
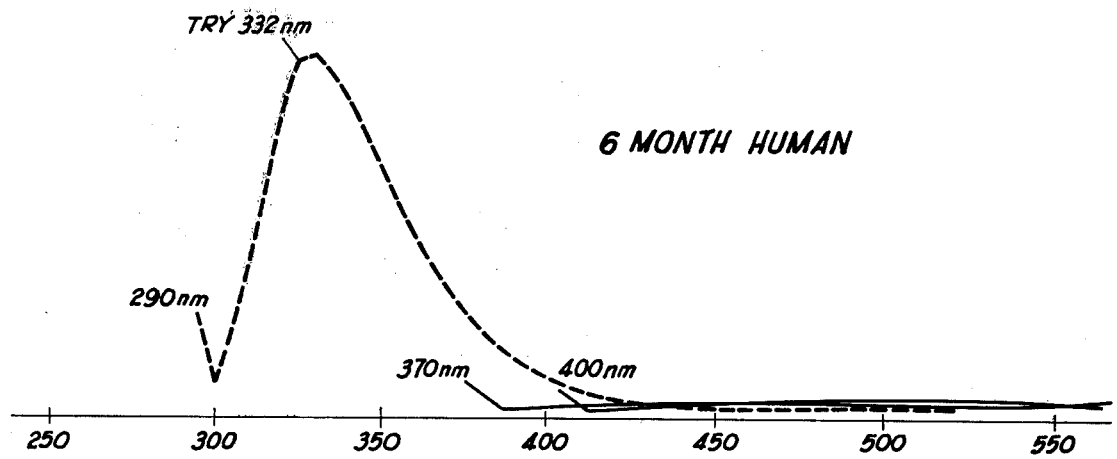
Figure 4:
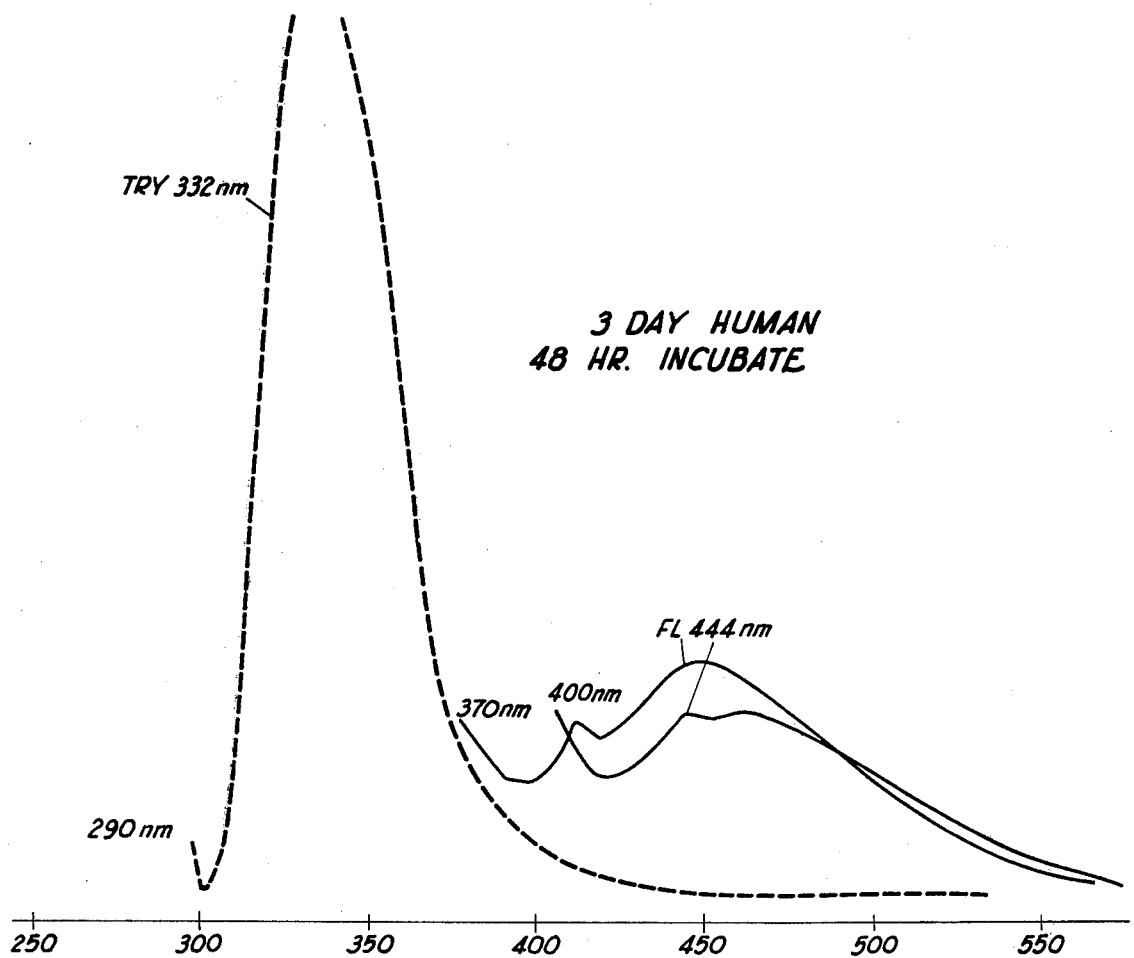
Figure 5:
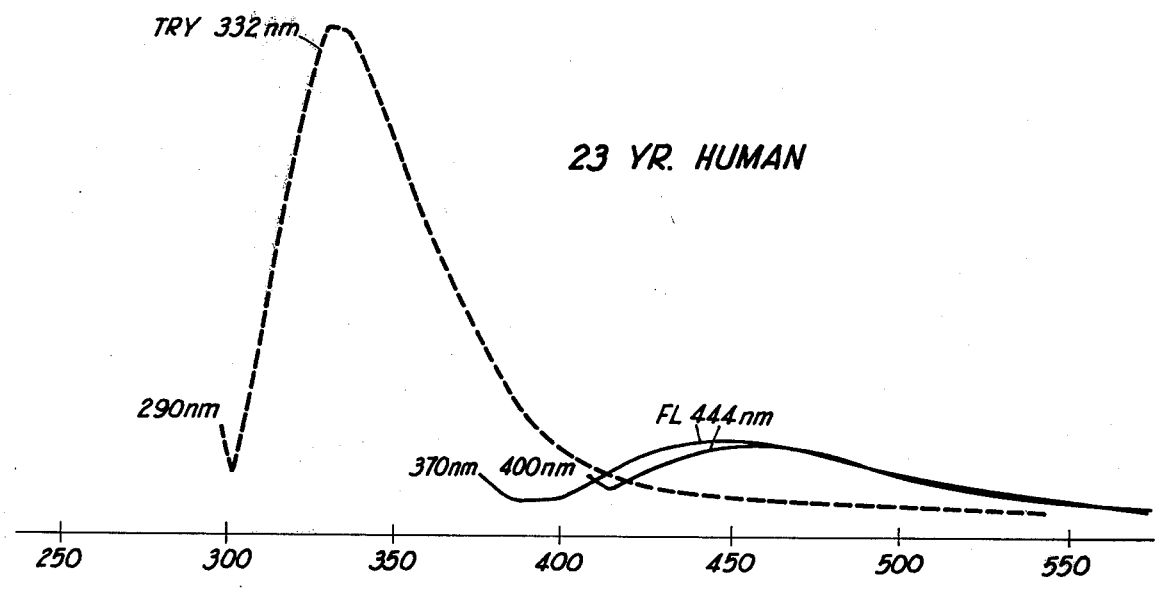
Figure 6:
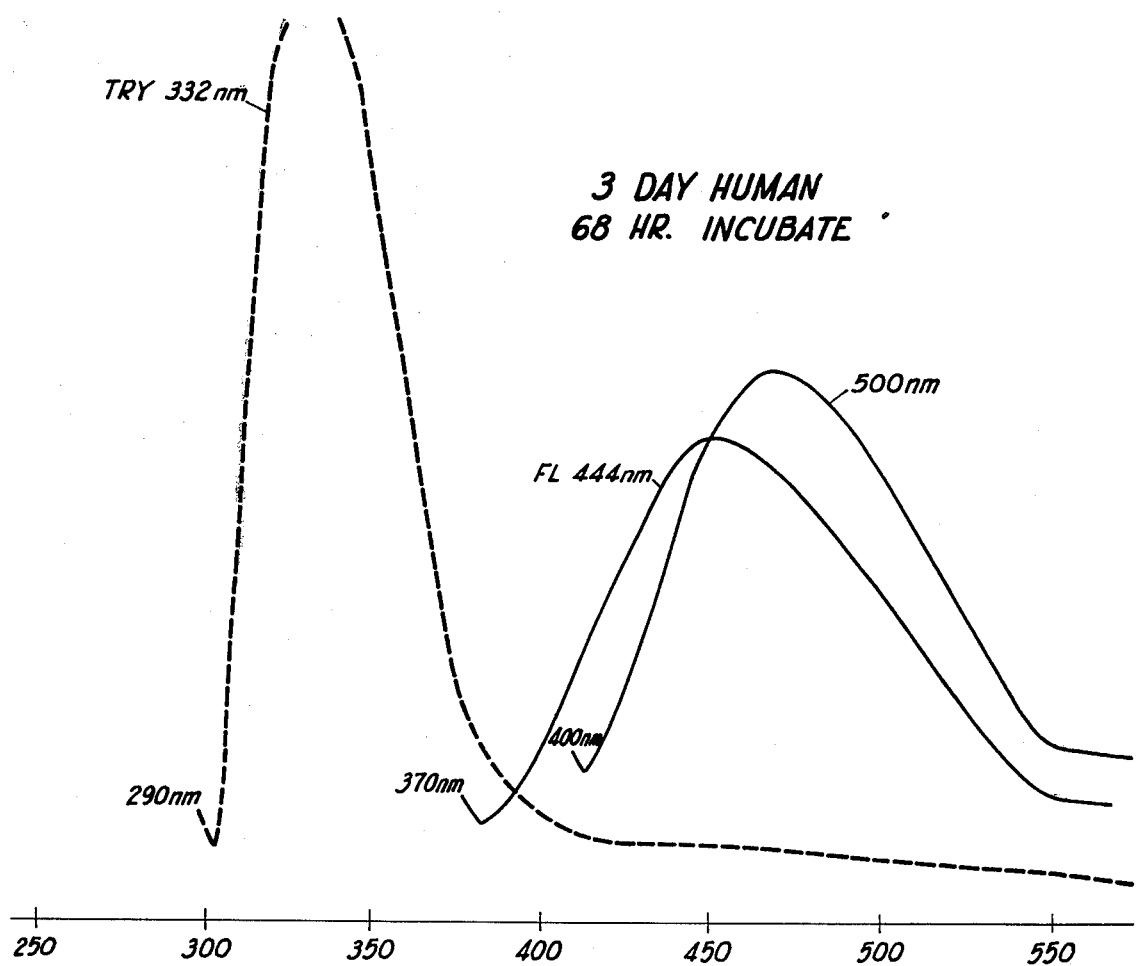
Figure 7:
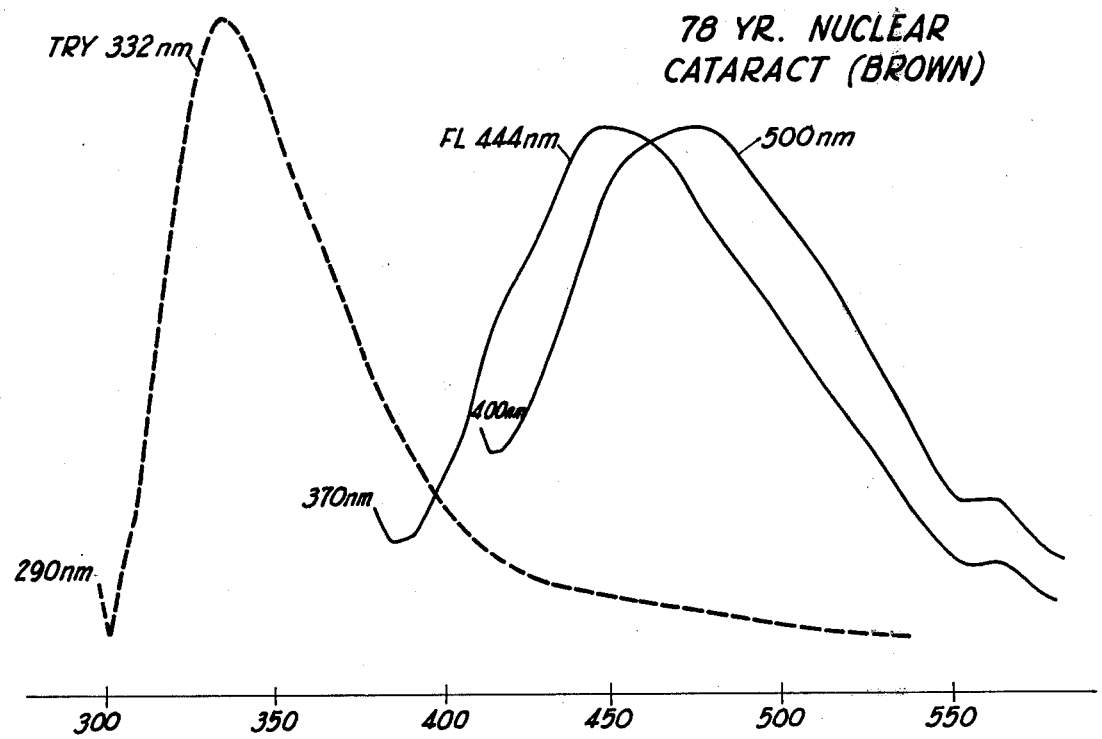
Figure 8:
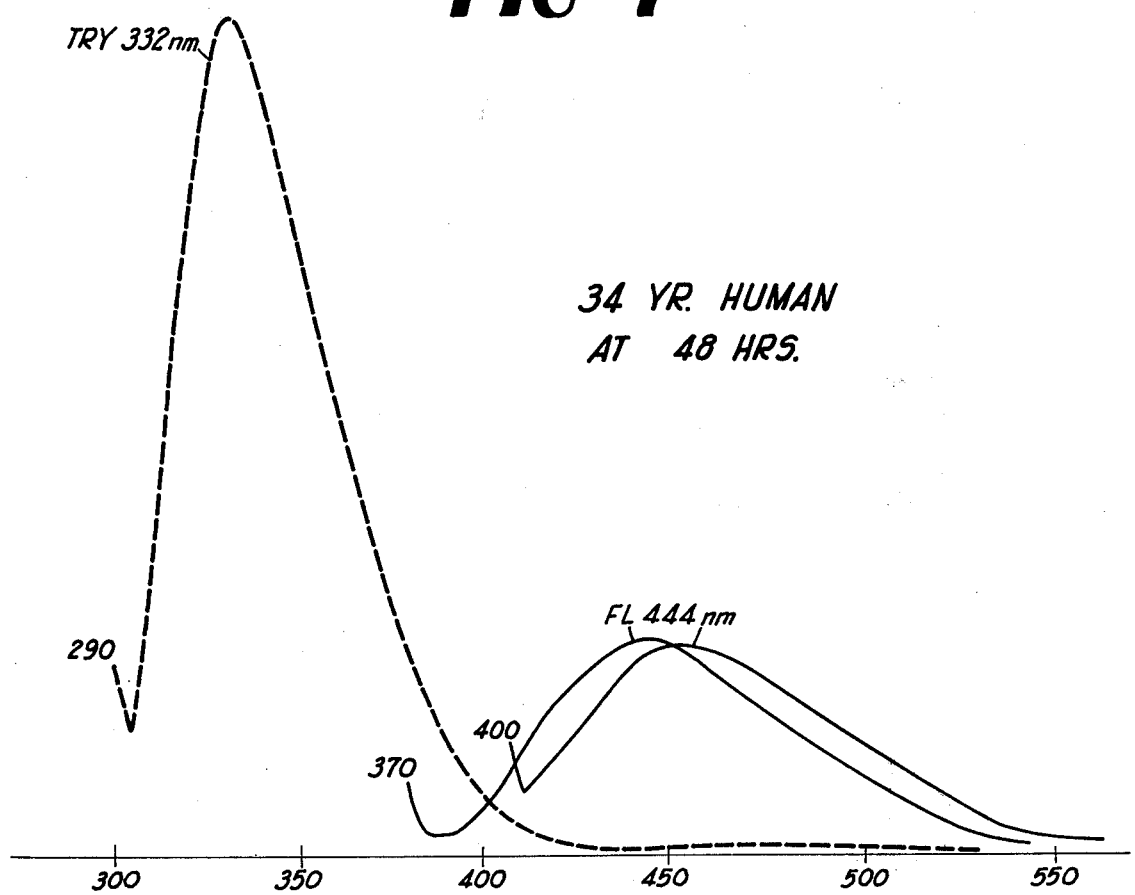

The results of in vitro incubation experiments with human lenses are shown in the fluorescence spectra of FIGS. 2 – 9. In FIGS. 2 and 3, no detectable 444 nm fluorogen could be demonstrated in the 3 day and 6 month old human lens; only intrinsic tryptophan (try 332) fluorescence was present (290 nm activation; 332 nm emission). When 3 day old human lenses are incubated for 48 and 68 hours, FIGS. 4 and 6, respectively, the resulting 444 nm fluorogen emission intensity (Fl 444 nm) is approximately equivalent to that of a 23 year old normal lens and a 78 year old nuclear cataract (FIGS. 5 and 7). At the same time, those 3 day old lenses which were previously completely transparent and colorless developed a deep yellow to brown color resembling lenses from much older individuals.

Similar incubations using normal human lenses in the 30 to 50 year age group also demonstrated a marked increase in the lens fluorogen so that the fluorescence spectra of these incubated lenses resembled the spectra of lenses from a considerably older age group, particularly with respect to the I (370/290) ratio. For example, the ratio for the 34 year old human lens incubated with AT alone for 48 hours is 0.28 (FIG. 8), while the lens from the opposite eye incubated with AT and UV for 48 hours showed an I (370/290) ratio of 0.54 (FIG. 9). As can be seen from FIG. 1, the effect of AT and UV on the 34 year old lens after 48 hours of incubation was to increase the ratio to that found in lenses from individuals of approximately 65 to 70 years of age. A similar marked increase in this ratio can be seen in the results obtained with the 48 and 68 hour 3 day human lens incubates (FIGS. 4 and 6). It should be noted that the increase in the ratio was inversely related to the age of the lens; the younger the lens the more marked the increase in the fluorogen following exposure to AT and UV (for example, the 3 day old lens and the 34 year old lens) while lenses derived from older individuals (50 to 60 year old lenses) also demonstrated an increase in the I (370/290) ratio but the effect was much less pronounced than with the younger lenses.

Furthermore, the foregoing spectra also demonstrate a bathochromic shift in the emission peak obtained with 400 nm activation In the normal lens, the 370 and 400 nm activation resulted in 444 emission peaks which were approximately equal. However, in those lenses exposed to AT and UV, there was a marked increase and bathochromic shift in the 400 nm activation fluorogen emission peak which could also be seen in the fluorescence spectra obtained from normal individuals in the age group above 50 or 60 years. Thus, there appears to be a second fluorogen emission peak close to 500 nm which is present in the aged lens and in the nuclear cataract but not in other forms of senile cortical cataracts. A similar bathochromic shift in the emission spectra from to 400 nm activation could be demonstrated in the rat lens incubation experiments.

The results of the experiments in which D,L-penicillamine was used as a free radical scavenger in order to prevent or diminish the induction of the fluorogen induced by ultraviolet light and aminotriazole are shown in FIGS. 10 and 11. When a 52 year old normal human lens is exposed to AT and UV for 31 hours, the resulting I (370/290) ratio equals 0.50 as compared with an average ratio in that age group of approximately 0.34. That is an approximate increase of 50% in this ratio due to AT plus UV exposure (FIG. 10). When the lens from the opposite eye was similarly exposed to AT plus UV for 31 hours but D,L-penicillamine was added to the incubation media at the same time, the resulting ratio was 0.22 (FIG. 11).

Similarly in the rat lens incubation studies, when a lens was exposed to AT plus UV plus D,L-penicillamine for 30 hours, the I (370/290) ratio was 0 while the lens from the opposite eye exposed to AT plus UV alone for 30 hours resulted in the development of a 444 nm emission fluorogen with an I (370/290) ratio of 0.23. Similarly, after 96 hours of incubation with AT and UV, the rat lens I ratio was 1.53 as compared with a ratio of 0.13 in the lens where D,L-penicillamine was added to the incubation media.

An in vivo study on post-weanling mouse lenses was also conducted. The normal 6 week old mouse showed no evidence of the fluorogen, while the lens from a 14 month old mouse did demonstrate the presence of this fluorogen. Lenses derived from the in vivo studies began to show the presence of a fluorogen one month after the beginning of the experiment and there was an increase in its level after 3 months at which time the experiment was terminated. It should be noted that control lenses from mice receiving 3-aminotriazole but shielded from ultraviolet light did not develop the fluorogen, nor did lenses from mice exposed to UV without AT develop the fluorogen during the experimental period.

Discussion

Ultraviolet light and ionizing radiation are capable of generating free radicals. It is generally accepted by many investigators that aging itself must at least in part be due to damage caused by radical reactions within tissues. An important effect of the induction of a free radical state in a compound by ultraviolet light (or other physical agents) is the fact that the resulting free radicals have considerably altered physical chemical properties leading to an alteration in their function. It has also been shown that proteins can be significantly altered by radical reactions with the aromatic amino acid residues in the proteins being particularly susceptible. Thus, the prolonged exposure of the ocular lens to long ultraviolet radiation could result in free radical formation and generation of one or more fluorogens in increasing concentration leading to a process of polymerization and insolubilization of the previously soluble lens protein fractions. UV-induced free radicals have been demonstrated in lens proteins and in the lens core.

The increase in the concentration of the water soluble lens proteins has been shown to occur as a definitive aging parameter and there is considerable evidence to indicate that this protein fraction derives from one or more of the previously soluble lens proteins. Previous studies have demonstrated that a fluorogen (with identical activation and emission spectra as reported in the foregoing experiments) could be isolated from the insoluble protein fraction of the lens and in some species from the soluble gamma crystalline fraction. The UV and fluorescence spectra obtained on this fluorogen extracted either by acid hydrolysis of the protein or following treatment of the protein with Pronase for 24 hours or more were identical. This would rule out the possibility that the fluorogen obtained following acid hydrolysis was a degradation product of tryptophan. Furthermore, peptide fingerprints of gamma crystalline were examined and an identical fluorogen was found to be present in one of the 21 peptides obtained following 6 hours tryptic digest. A fluorogen with similar characteristics has also been reported by other investigators with a similar direct relationship between aging of the lens and the increase in the fluorogen content and the insoluble lens protein levels. The presence of similar fluorogens in lenses derived from various species (for example, the lens of omnivorous man and herbivorous rabbit) suggest their source is not dietary.

A considerable amount of evidence, however, has now accumulated to indicate that ultraviolet light plays a significant if not primary role in the generation of this fluorogen. The fluorogen is generated photochemically with tryptophan as the prime UV light absorbing species; this conclusion is supported by the observation that the photochemical production of fluorogen is accompanied by a decrease in tryptophan fluorescence. The specific identity of the fluorogen remains to be defined although it appears to be of small molecular weight (under 600) and is tightly bound to one or more of the lens protein fractions. There is at present agreement among several investigators that this fluorogen could be the result of a photo-chemical degradation of tryptophan which would produce a condensation product of anthranalic acid resulting in the formation of a tricyclic compound (mol. wt. 301) with fluorescence and UV spectra identical to those previously reported. The proposal of protein tryptophan depletion via oxidation, resulting in protein pigmentation correlates with the above described observations regarding the inverse relationship between tryptophan fluorescence intensity and the fluorogen emission intensity.

The fluorogen probably exerts its effect by playing a significant role in the polymerization process of certain water soluble lens proteins to give rise to much larger molecular weight aggregates. (An example of such a mechanism can be found in the generation of bityrosine from tyrosine and its role in the formation of the keratoproteins constituting the shells of certain Crustaceans.) This possibility correlates well with what is known of the conformation of the lens proteins; ORD and CD studies have indicated that the major conformation of the alpha and gamma crystalline of the lens is the beta structure and Raman spectroscopy suggests an anti-parallel beta-pleated structure for a major portion of the lens proteins.

The compound 3-aminotriazole (AT), which is a catalase inhibitor, can be employed in simple lens incubation systems to significantly decrease the concentration of glutathione in the lens. The foregoing experiments have demonstrated that lenses incubated with AT and exposed to ultraviolet light at approximately 280 – 340 nm wavelength for varying periods of time ranging from 4 to 96 hours will develop a fluorogen and yellow color of increasing intensity. The presence of at least one specific fluorogen can be demonstrated in increasing concentration directly related to the duration of the incubation. It should be noted that control lenses were run concurrently with all these experiments; when the lenses were exposed only to 3-aminotriazole and shielded from ultraviolet light, no fluorogen could be generated nor did the lens show any change in color. Experiments in which the lens incubates were exposed only to ultraviolet light for periods of time above 24 hours did show a very slight formation of this fluorogen but at a level approximately 10% of that when 3-aminotriazole was included in the incubation mixture.

It is interesting to note that the ocular lens contains one of the highest concentrations of glutathione of all body tissues (as well as ascorbic acid). Both of these compounds can function as free radical scavengers, particularly glutathione. (Glutathione cannot be administered into the body to perform its free radical scavenging function because it oxidizes immediately.) The yellow pigmentation is confined mainly to the lens nucleus since there is an insufficient concentration of free radical scavenger in this region to abort the photochemical degradation reaction. Thus, the lens nucleus is particularly susceptible to UV radiation since it has a relative lack of the normal free radical scavenger present in the lens (glutathione) as compared with the lens cortex; this becomes particularly pronounced as the lens ages. Hence, the action of 3-aminotriazole in the in vitro and in vivo experiments appears to be that of decreasing the concentration of glutathione in the lens so that insufficient amounts of an important free radical scavenger are present while the lens is being exposed to the ultraviolet radiation. Since D,L-penicillamine has been shown to be a very effective free radical scavenger, the in vitro incubation studies which were performed with human and rat lenses demonstrate that D,L-penicillamine does have a very significant effect in markedly decreasing or eliminating the relative emission intensity of the 444 nm fluorogen in animal lenses as compared with the incubates in which the lenses were exposed to ultraviolet and 3-aminotriazole only. Since D,L-penicillamine is less toxic and more soluble than other anti-oxidants that have been employed, this free radical scavenger is more effective in the in vivo systems as well.

One of the methods of administering to the eye the free radical scavenging agent (D,L-penicillamine) is by exposing artificial ocular lenses (such as soft hydrophylic corneal contact lenses, soft hydrophylic molded corneal scleral contact lenses, and ocular bandage type of lenses, either corneal or corneal scleral lenses) to a solution containing the agent so that artificial lens would accumulate a sufficient amount of the agent that when the artificial lens was applied to the animal eye, the agent would be absorbed through the cornea and aqueous humor and into the ocular lens. The agent would then prevent or inhibit free radical damage which the ocular lens itself over a period of years could no longer counteract.

In the artificial lens bathing or cleansing solution approach, the amount of the agent that would be incorporated on the artificial lens would, of course, depend on the concentration of the agent that would be put into the solution. (The "on the artificial lens" includes the solution being absorbed "into" the lens, as well.) If the agent utilized is D,L-penicillamine, then a 100% or saturated solution of the penicillamine in physiological saline can be utilized in which to soak the artificial lens. Not only would D,L-penicillamine be utilized in the solution for its ability as a free radical scavenger but also for its use as a chelating agent, thereby replacing ethylenedinitrilotetracetic acid (EDTA) which is a common additive in soft contact lens solutions for its chelating properties.

The solution can also include an antiseptic material, and would be isotonic with animal tears. It has been found that the sodium salt of ethylmercurithiosalicylic acid (thimerosol) is effective in an amount in the solution ranging from 0% to 0.1% by weight, with the preferred concentration being 0.05%. Laboratory experiments with the hydrophylic lens manufactured by National Patent Development Corporation and by Bausch & Lomb have shown that this type of lens does not concentrate thimerosol nor does it concentrate benzalkonium chloride or chlorbutanol in solutions in which those materials or preservatives are present in concentrations less than 0.1%. The experiments involved soaking such lenses in solutions ranging from 0.05 to 0.5% of the individual preservatives for periods of time up to 72 hours, at which time the lenses were removed. Whatever preservative remained in the lens was leached out and measured. The experiments proved conclusively that when such lenses were soaked in concentrations of less than 0.1%, there was an infinitesimal amount of preservative retained in the lens, and there was no evidence of any concentrating effect and that the very slight amount present in such lenses would be insufficient to cause any ocular damage.

A composition of the solution could be D,L-penicillamine in concentration ranging from between 20 and 40%, physiological saline and 0.05% thimerosol. The pH of the solution should be maintained between 6 and 8. The soft hydrophylic lenses can be soaked in this solution overnight and then can be safely worn without any care required. The artificial lens could also be boiled daily in the penicillamine solution for sterilization purposes.

Aside from the antiseptic and antibacterial activity of such a cleansing solution, it would have the advantage of containing a high concentration of D,L-penicillamine which could be absorbed into the ocular lens and provide a constant source of potent free radical scavenger, thereby functioning to protect the lens from the effects of the ultraviolet radiation (320 - 380 nm) that the lens is constantly exposed to throughout life.

Another method of administering an agent for treating the animal ocular lens for the formation of nuclear cataracts is to incorporate the agent within a sustained timed-release carrier and placing the carrier within the inferior cul de sac of the eye so that the agent would be released at a constant and continuous rate. Such ocular administering of the agent could be in a hydrophylic or hydrophylic-hydrophobic gel or an insert or an ointment. If D,L-penicillamine is utilized, the concentration released into the eye would range from 1 - 10 mg/24 hours.

D,L-penicillamine can also be administerd orally or parenterally, with the dosage being no more than 250 mg/24 hours.

Further, D,L-penicillamine can be administered in eye drop form in a solution comprising D,L-penicillamine and methylcellulose.

What is claimed is:

1. A method of administering an agent to animal ocular lenses for the treatment of nuclear cataracts therein, comprising the steps of:
   a. preparing a solution which is isotonic with animal tears and which includes physiological saline and an effective amount of said agent to form a saturated solution, said agent being D,L-penicillamine;
   b. exposing artificial ocular contact lenses to said solution for a sufficient period of time wherein said agent is retained on said lenses; and
   c. placing said exposed artificial lenses on the ocular cornea and/or cornea and sclera whereby said agent enters said ocular lenses.

2. A method as claimed in claim 1 wherein said solution further includes an antiseptic material in the range of 0% to 0.5% by weight.

3. A method as claimed in claim 2 wherein the preferred amount of said material is 0.05% by weight.

4. A method as claimed in claim 3 whereby said material is the sodium salt of ethylmercurithiosalicylic acid.

5. A method of administering an agent to animal ocular lenses for the treatment of the formation of nuclear cataracts therein, comprising the steps of incorporating an effective amount of D,L-penicillamine in a sustained release carrier and placing said carrier within the inferior cul de sac of the eye.

6. A method as claimed in claim 5 wherein said carrier releases said agent at a rate of from 1 - 10 mg/24 hours.

7. An ocular lens treatment composition for animals, comprising an effective amount of D,L-penicillamine and a sustained release carrier therefor in a form for placement in the inferior cul de sac of the eye for the treatment of nuclear cataracts in said lens.

8. A method of treating nuclear sclerosis in animals comprising the step of administering to the ocular lens an effective amount of D,L-penicillamine.

* * * * *